US008096655B2

(12) United States Patent
Daphna

(10) Patent No.: US 8,096,655 B2
(45) Date of Patent: Jan. 17, 2012

(54) HYPER-OSMOTIC EYE CONTACT LENS

(75) Inventor: Ofer Daphna, Ashkelon (IL)

(73) Assignee: Eyeon Medical Ltd., Givat Ram, Jereusalem (IL)

( * ) Notice: Subject to any disclaimer, the term of this patent is extended or adjusted under 35 U.S.C. 154(b) by 0 days.

(21) Appl. No.: 12/809,623

(22) PCT Filed: Dec. 17, 2008

(86) PCT No.: PCT/IL2008/001635

§ 371 (c)(1), (2), (4) Date: Jun. 21, 2010

(87) PCT Pub. No.: WO2009/078021

PCT Pub. Date: Jun. 25, 2009

(65) Prior Publication Data

US 2010/0321631 A1 Dec. 23, 2010

(51) Int. Cl.
*G02C 7/04* (2006.01)

(52) U.S. Cl. ................................ 351/160 R; 361/160 H

(58) Field of Classification Search .............. 351/160 R, 351/160 H, 161, 162

See application file for complete search history.

(56) References Cited

U.S. PATENT DOCUMENTS

| | | | | |
|---|---|---|---|---|
| 4,099,859 | A | 7/1978 | Merrill | |
| 4,166,255 | A | 8/1979 | Graham | |
| 4,466,705 | A * | 8/1984 | Michelson | 623/5.16 |
| 4,597,965 | A | 7/1986 | Holly | |
| 5,958,443 | A | 9/1999 | Viegas et al. | |
| 2007/0122450 | A1 * | 5/2007 | Osio Sancho | 424/428 |

* cited by examiner

*Primary Examiner* — Scott J Sugarman

(74) *Attorney, Agent, or Firm* — Dekel Patent Ltd.; David Klein

(57) ABSTRACT

A hyper-osmotic contact lens designed to compensate for an unhealthy edematous state for treating corneal edema.

10 Claims, 3 Drawing Sheets

HYPER-OSMOTIC EYE CONTACT LENS

FIELD OF THE INVENTION

The present invention relates generally to contact lenses and in particular to contact lenses designed to compensate for an over-hydrated, edematous cornea.

BACKGROUND OF THE INVENTION

The quality of the eye's sensory function greatly depends on the qualities of light conduction through the cornea and through the lens, and also the optical qualities of these organs and the transparency of the cornea and the eye lens, as well as other factors.

Experts in the field of ophthalmology know that corneal transparency generally depends on the ability of the cornea to remain in a dehydrated state. The cornea dehydrated state is affected by several interdependent factors, the most important of which is an active pump present in the deepest cell layer of the cornea, the endothelium. Any disruption of the endothelial function beyond a certain level as a result of surgery, trauma, infection, or congenital predisposition results in influx of water to all layers of the cornea thus distorting its transparency. The morbidity of this situation is not only a significant decrease in vision, but also at an advanced state may result in significant pain and scars, a situation known as bullous keratopathy.

Another important physiological mechanism for dehydrating the cornea is the evaporation of water from the tear film while the eye is open during wakefulness. Dehydration works by water evaporating from the tear film, which leaves behind a more concentrated solution at the surface of the eye, causing the tear film to be more hypertonic. The hypertonic tear film draws more water by osmosis from the cornea itself; the opposite is true during the night. There are some hypertonic solution eye drops available in the market to augment this mechanism but unfortunately their action is short lived due to the blinking of the eyelids.

In contemporary medical science there is no genuinely conservative treatment for an unhealthy edematous state, and most patients end up in the long waiting line for corneal transplants. There is therefore a need for a device and method to alleviate the unhealthy edematous state.

SUMMARY OF THE INVENTION

The present invention relates to hyper-osmotic contact lens, designed to compensate for an unhealthy edematous cornea.

The hyper-osmotic contact lens is designed to treat corneal edema. The hyper-osmotic contact lens absorbs fluid from an edematous cornea by the force of an osmotic gradient. The hyper-osmotic contact lens is designed as a microcontainer with walls that are thin relative to its general dimensions, and is shaped as a lens with an anterior wall and a posterior wall, with part of the posterior wall serving as a water permeable membrane, and a hyper-osmotic transparent medium such as dry hydrogel or solution such as glycerol, salts, etc. The refractive property of the lens can be taken into account according to patient refraction.

The anterior microcontainer wall of the hyper-osmotic contact lens is made of a material which is water impermeable but oxygen permeable, such as silicone, silicone hydrogel, etc., and prevents water osmosis. The posterior wall of the hyper-osmotic contact lens, the area in which the cornea and the contact lens overlap, is made of selective water permeable membrane. In this area, water from the edematous cornea can flow out of the cornea into the hyper-osmotic chamber by the force of osmosis, thus dehydrating the cornea itself. Since most of the surface area of the contact lens is water impermeable, and only a small part of it which is in contact with the cornea is water permeable, the hyper osmotic contact lens is able to dehydrate the cornea without eliminating too much tear film solution from the eye thus preventing dehydration of the eye itself.

The hyper-osmotic contact lens is slowly filled with water, thus becoming isotonic with its environment. The hyper-osmotic contact lens could be "recharged" (set back to hyper-osmotic state) by being immersed in a hyper-osmotic solution.

There is provided in accordance with an embodiment of the present invention a contact lens including a hyper-osmotic chamber bounded by a posterior wall and an anterior wall and containing therein a hyper-osmotic substance, wherein the anterior wall is made of a water resistant material that prevents water osmosis and a posterior permeable portion of the posterior wall is made of a water permeable material, wherein when the posterior wall is mounted on a cornea, water from the cornea flows out of the cornea through the posterior wall into the hyper-osmotic chamber by osmosis due to an osmotic pressure gradient between the cornea and the hyper-osmotic chamber.

In accordance with an embodiment of the present invention, the anterior wall is impermeable to passage of water. Alternatively, the anterior wall includes an anterior permeable portion which is permeable to passage of water. In accordance with an embodiment of the present invention, the posterior permeable portion does not span an entire area of the posterior wall. Alternatively, the posterior permeable portion spans an entire area of the posterior wall.

There is also provided in accordance with an embodiment of the present invention a method for compensating for an unhealthy edematous state of the cornea, the method including providing a contact lens including a hyper-osmotic chamber bounded by a posterior wall and an anterior wall and containing therein a hyper-osmotic substance, wherein the anterior wall is made of a water resistant material that prevents water osmosis and a posterior permeable portion of the posterior wall is made of a water permeable material, and mounting the posterior wall on a cornea so that water from the cornea flows out of the cornea through the posterior wall into the hyper-osmotic chamber by osmosis due to an osmotic pressure gradient between the cornea and the hyper-osmotic chamber.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
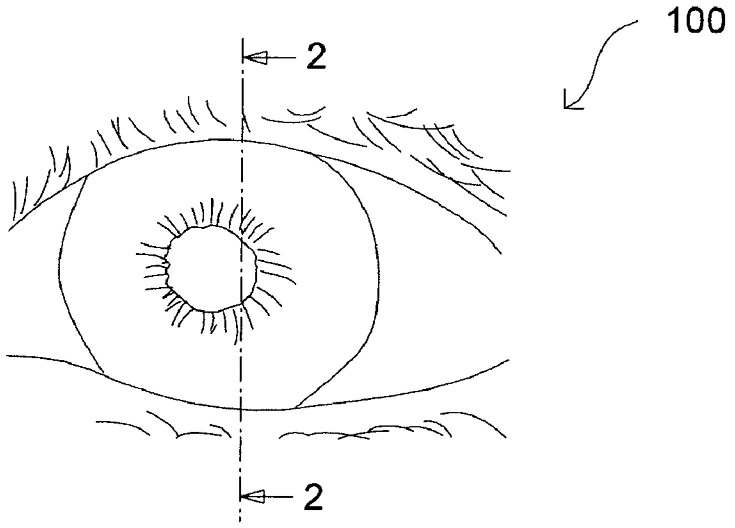
FIG. 1 is a front view schematic illustration of a human eye.
Figure 2:
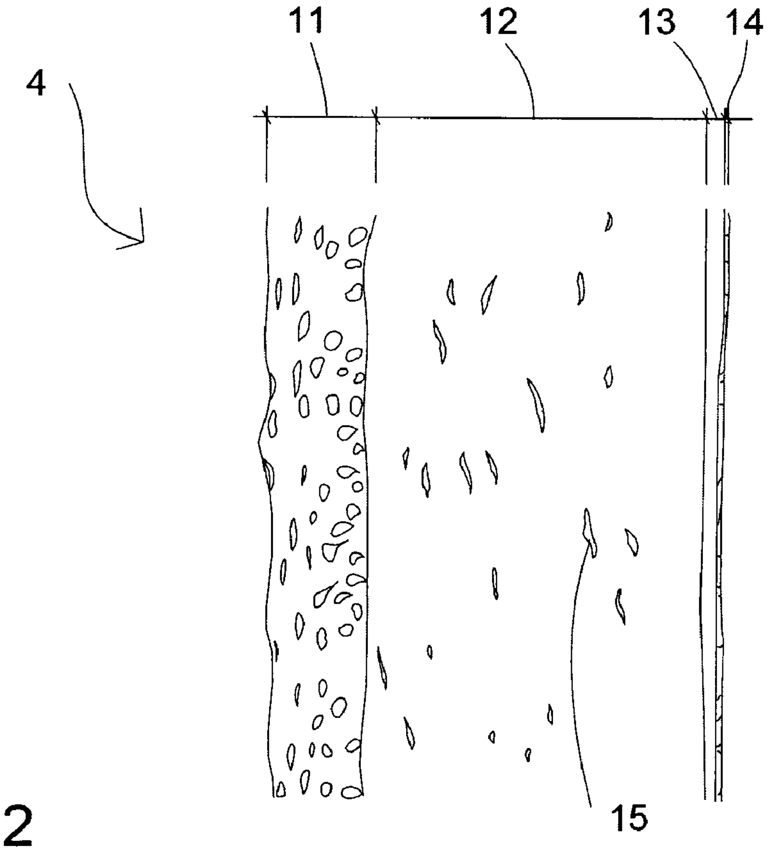
FIG. 2 is a schematic cross sectional view of a human eye cornea, taken along lines 2-2 in FIG. 1.

Reference is now made to FIG. 1, which is a front view schematic illustration of a human eye 100, and to FIG. 2, which is a schematic cross sectional view of layers of a human eye cornea 4, on section plane 2-2. The most anterior layer in contact with the outside air is the anterior corneal epithelium stratified squamous layer 11, after which come the corneal stroma layer 12, the posterior limiting lamina layer 13, and the posterior endothelium layer 14.

The corneal stroma layer 12 contains keratocyte nuclei 15. As noted, the corneal transparency generally depends on the ability of the cornea to remain in a dehydrated state which is affected by several interdependent factors, the most important of which is an active pump present in the deepest cell layer of the cornea, the endothelium layer 14.

Figure 3:
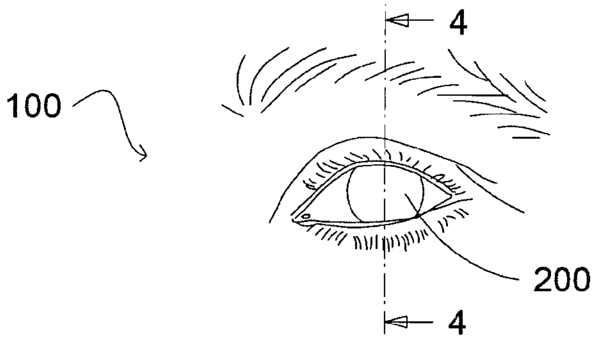
FIG. 3 is a simplified front view illustration of a hyper-osmotic eye contact lens, constructed and operative in accordance with an embodiment of the present invention, mounted on a human eye.
Figure 4:
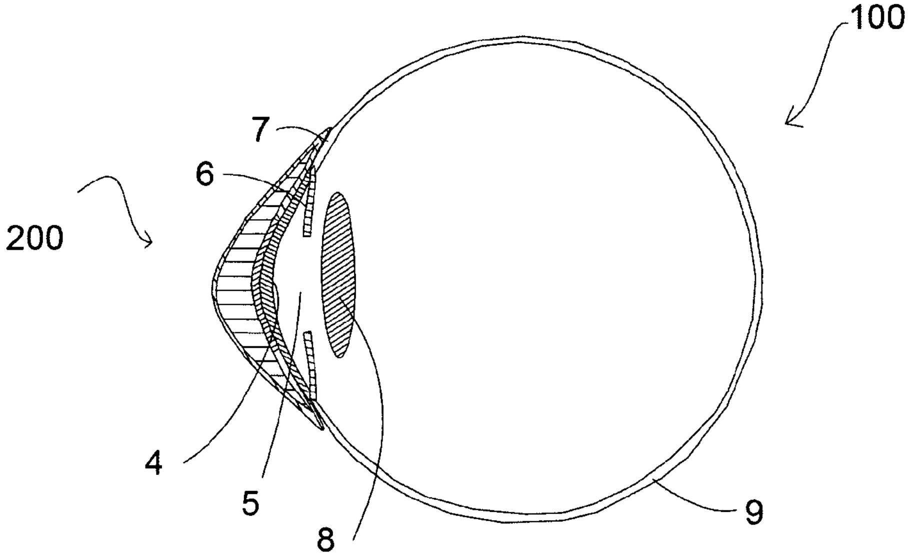
FIG. 4 is a schematic cross sectional view of the hyper-osmotic eye contact lens and of a human eye on which it is mounted, taken along section line 4-4 in FIG. 3.

Reference is now made to FIGS. 3 and 4, which illustrate an exemplary embodiment of a hyper-osmotic eye contact lens 200, according to the present invention, mounted on a human eye 100. FIG. 4 illustrates different organs of the human eye, namely, cornea 4, anterior chamber 5, iris 6, sclera 7, lens 8, and conjunctiva 9. A hyper-osmotic eye contact lens 200 is mounted on the anterior of the eye.

Figure 5:
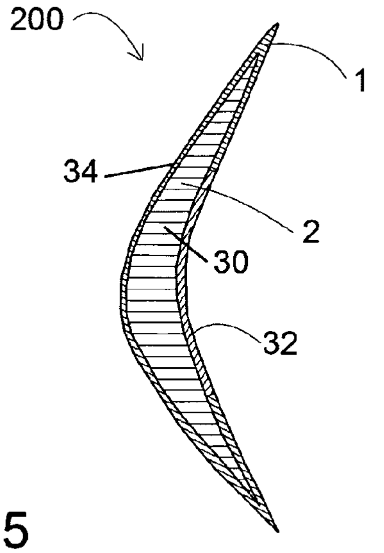
FIG. 5 is a simplified cross sectional view of the hyper-osmotic eye contact lens, in accordance with an embodiment of the present invention.

Reference is now made to FIG. 5, which illustrates a cross sectional view of contact lens 200. Contact lens 200 includes a hyper-osmotic chamber 30 bounded on the posterior side (i.e., the side that contacts the cornea) by a posterior wall 32 and on the anterior side by an anterior wall 34. Anterior and posterior walls 32 and 34 are joined at a peripheral edge 1. The anterior wall 34 of the hyper-osmotic contact lens 200 is made of a material that is water impermeable but oxygen permeable, such as but not limited to, silicone, silicone hydrogel, etc., thereby preventing water osmosis therethrough.

The posterior wall 32 is made of a selectively water permeable material. Examples of suitable water permeable materials include, but are not limited to, hydrogel or methafilcon (methafilcon comprises HEMA ((2-hydroxyethyl methacrylate) and methacrylic acid crosslinked with EDGMA (ethyleneglycol dimethacrylate)), or even silicone with small holes drilled or otherwise formed therethrough. How much of posterior wall 32 is permeable is discussed below with reference to FIG. 6*c*. Water from the edematous cornea can flow out of the cornea through posterior wall 32 into the hyper-osmotic chamber 30 by osmosis, thus dehydrating the cornea.

The internal material in hyper-osmotic chamber 30 is a hyper-osmotic substance 2, which may be a hyper-osmotic transparent medium such as, but not limited to, dry hydrogel, etc., or solution such as, but not limited to, glycerol, salt solution, etc., which also has suitable refraction and transparency properties, which may be selected for modifying vision of a patient.

This structure enables hyper-osmotic eye contact lens 200 to serve as a pump pumping water from the cornea and fulfill its purpose of treating corneal edema. To enable hyper-osmotic eye contact lens 200 to pump a significant amount of water, it needs to be of sufficiently large volume, and therefore it needs to be thick enough in the middle or alternatively thin in the middle and thick at its edge as in the embodiment of FIG. 7. Hyper-osmotic eye contact lens 200 has a suitable volume to enable functioning for a sufficient duration until it is full. Accordingly, contact lens 200 may be used for daily treatment, partial daily treatment or overnight treatment, or any other treatment period which is needed for the patient treatment when it is mounted upon a cornea in an edematous state. Contact lens 200 may be sized to fit over the cornea to the limbus, or alternatively may extend over the limbus.

In general, the geometry of contact lens 200 may be selected for the particular patient. For example, the geometry of posterior wall 32 may be selected for any keratometry reading to create a steep fit, flat fit (flat K) or any combination thereof. The optical properties of the hyper-osmotic substance 2, the optical properties of the lens and properties of the lens material (e.g., hard, soft, etc.), and the optical effect of the interface between the lens and the measured topography of the cornea are just some of the factors which can be taken into consideration for determining the shape of the lens.

The presence of hyper-osmotic substance 2 creates a molecular concentration gradient and thus osmotic pressure gradient between the cornea and hyper-osmotic chamber 30. The osmotic pressure gradient results in a net flow of fluid from the cornea into hyper-osmotic chamber 30. The lens 200 can be constructed to reach a steady state net flow of fluid or not to reach a steady state, as is now explained.

Figure 6A:
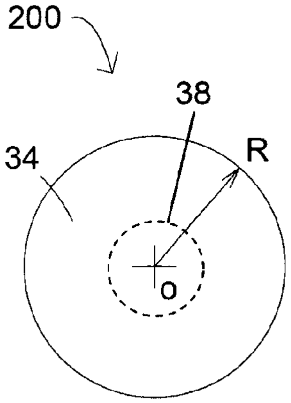
FIGS. 6*a*, 6*b* and 6*c* are respectively simplified front view, side view and rear view illustrations of the hyper-osmotic eye contact lens, in accordance with an embodiment of the present invention.
Figure 6B:
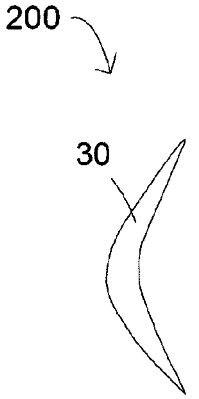
Figure 6C:
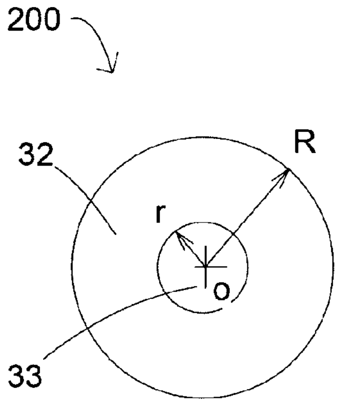

Reference is now made to FIGS. 6*a*-6*c*. FIG. 6*a* illustrates anterior wall 34, which is shaped as a circle with center o and radius R. FIG. 6*c* illustrates posterior wall 32. The area of posterior wall 32 which is permeable is shown as a circle with a radius r (referred to as posterior permeable portion 33). In accordance with one embodiment of the invention, r<R meaning the area outside the circle with radius r on posterior wall 32 is impermeable to passage of water. In accordance with another embodiment of the invention, r=R meaning the entire posterior wall 32 is permeable to passage of water. Posterior permeable portion 33 may be non-circular or other shapes as well.

In accordance with one embodiment of the invention, the entire anterior wall 34 is impermeable to passage of water. In such a case, the molecular concentration inside hyper-osmotic chamber 30 and the molecular concentration outside hyper-osmotic chamber 30 at the cornea will eventually equalize, i.e., reach steady state.

In accordance with another embodiment of the invention, a portion of anterior wall 34, shown in broken lines 38 in FIG. 6*a*, is permeable to passage of water (referred to as anterior permeable portion 38). Anterior permeable portion 38 may be circular, non-circular or other shapes as well. In such a case, the molecular concentration inside hyper-osmotic chamber 30 and the molecular concentration outside hyper-osmotic chamber 30 at the cornea will never equalize, i.e., will not reach steady state. This means that the fluid will continuously flow from the cornea into hyper-osmotic chamber 30 and flow out to the environment via anterior permeable portion due to evaporation 38. The contact lens 200 can be custom made to suit the needs of the patient.

Figure 7:
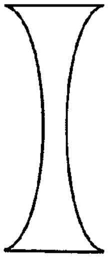
FIG. 7 is a simplified side view illustration of a hyper-osmotic eye contact lens, in accordance with another embodiment of the present invention.

In the embodiment illustrated in FIG. 5, hyper-osmotic eye contact lens 200 is shaped as a standard concave-convex positive lens, meaning it is concave towards the anterior, convex towards the posterior, and is relatively thick in the center and narrow at the circumference. For example, the concave anterior wall may be disposed at a distance of at least one tenth of a millimeter from the convex posterior wall. Alternatively, as shown in FIG. 7, the contact lens may be a negative lens (concave-concave).

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A contact lens comprising:

a hyper-osmotic chamber bounded by a posterior wall and an anterior wall and containing therein a hyper-osmotic substance, wherein said anterior wall is made of a water resistant material that prevents water osmosis and a posterior permeable portion of said posterior wall is made of a water permeable material, wherein when said posterior wall is mounted on a cornea, water from the cornea flows out of the cornea through said posterior wall into said hyper-osmotic chamber by osmosis due to an osmotic pressure gradient between the cornea and said hyper-osmotic chamber.

2. The contact lens according to claim 1, wherein said anterior wall is impermeable to passage of water.

3. The contact lens according to claim 1, wherein said anterior wall comprises an anterior permeable portion which is permeable to passage of water.

4. The contact lens according to claim 1, wherein said posterior permeable portion does not span an entire area of said posterior wall.

5. The contact lens according to claim 1, wherein said posterior permeable portion spans an entire area of said posterior wall.

6. The contact lens according to claim 1, wherein said contact lens is shaped as a concave-convex positive lens.

7. The contact lens according to claim 1, wherein said contact lens is shaped as a concave-concave negative lens.

8. The contact lens according to claim 1, wherein said hyper-osmotic substance has refraction and transparency properties selected for modifying vision of a patient.

9. The contact lens according to claim 1, wherein said anterior wall is oxygen permeable.

10. The contact lens according to claim 1, wherein a surface area of said anterior wall is greater than a surface area of said posterior wall.

* * * * *

UNITED STATES PATENT AND TRADEMARK OFFICE

CERTIFICATE OF CORRECTION

PATENT NO. : 8,096,655 B2
APPLICATION NO. : 12/809623
DATED : January 17, 2012
INVENTOR(S) : Ofer Daphna It is certified that error appears in the above-identified patent and that said Letters Patent is hereby corrected as shown below:

On the Title Page: Item (73) Assignee:

The correct assignee is as follows:

MOR RESEARCH APPLICATIONS LTD., 38 Habarzel Street, Tel Aviv 69710, Israel

Signed and Sealed this
Twenty-first Day of August, 2012

David J. Kappos
*Director of the United States Patent and Trademark Office*